(12) United States Patent
Browder et al.

(10) Patent No.: US 8,412,029 B2
(45) Date of Patent: Apr. 2, 2013

(54) FRAGRANCE PRODUCING LIGHTING DEVICE

(75) Inventors: John Browder, Argyle, TX (US); Matthew Kowalec, Coto De Caza, CA (US); Alan Rushing, Irvine, CA (US); Brett Moody, Chicago, IL (US)

(73) Assignee: IDC Enchanted Lighting Company, LLC, Roanoke, TX (US)

( * ) Notice: Subject to any disclaimer, the term of this patent is extended or adjusted under 35 U.S.C. 154(b) by 0 days.

(21) Appl. No.: 13/280,055

(22) Filed: Oct. 24, 2011

(65) Prior Publication Data

US 2012/0093491 A1 Apr. 19, 2012

Related U.S. Application Data

(63) Continuation-in-part of application No. 13/171,730, filed on Jun. 29, 2011.

(60) Provisional application No. 61/434,185, filed on Jan. 19, 2011.

(51) Int. Cl.
*A61M 16/00* (2006.01)

(52) U.S. Cl. ......... 392/390; 392/386; 392/391; 422/125

(58) Field of Classification Search ................. None
See application file for complete search history.

(56) References Cited

U.S. PATENT DOCUMENTS

| | | | | |
|---|---|---|---|---|
| 2,207,889 A * | 7/1940 | Kingman | ...................... | 392/393 |
| 3,288,556 A * | 11/1966 | Weber, III | ...................... | 422/125 |
| 4,346,059 A * | 8/1982 | Spector | ...................... | 422/125 |
| 4,571,485 A * | 2/1986 | Spector | ...................... | 392/390 |
| 4,647,428 A * | 3/1987 | Gyulay | ...................... | 422/4 |
| 4,931,224 A * | 6/1990 | Holzner | ...................... | 261/30 |
| 5,147,582 A * | 9/1992 | Holzner et al. | .................. | 261/30 |
| 5,431,885 A * | 7/1995 | Zlotnik et al. | .................. | 422/122 |
| 5,547,721 A * | 8/1996 | Kuo | .............. | 428/34.1 |
| 5,939,033 A * | 8/1999 | Kendall et al. | .................. | 422/305 |
| 6,080,367 A * | 6/2000 | Lin | ................... | 422/124 |
| 6,099,137 A * | 8/2000 | McCormack et al. | .......... | 362/96 |
| 6,349,168 B1 * | 2/2002 | Jaworski | ...................... | 392/392 |
| 6,381,408 B1 * | 4/2002 | Jaworski et al. | .............. | 392/392 |
| 6,482,365 B1 * | 11/2002 | Soller | ........................ | 422/126 |
| 6,719,443 B2 | 4/2004 | Gutstein et al. | | |
| 6,775,470 B2 * | 8/2004 | Zobele et al. | .................. | 392/390 |
| 6,960,320 B1 * | 11/2005 | Smith et al. | ....................... | 422/5 |
| D517,673 S * | 3/2006 | Yamamoto et al. | .......... | D23/366 |
| 7,083,162 B2 * | 8/2006 | He et al. | ....................... | 261/142 |
| 7,132,084 B1 | 11/2006 | Roumpos | | |
| 7,625,578 B2 * | 12/2009 | Davis et al. | ..................... | 424/409 |
| 7,670,035 B2 | 3/2010 | Tsai | | |
| 7,713,488 B2 * | 5/2010 | Harris et al. | ................... | 422/122 |
| 7,850,327 B2 | 12/2010 | Campbell et al. | | |
| 8,137,629 B2 * | 3/2012 | Faber et al. | .................... | 422/120 |
| D667,101 S * | 9/2012 | Browder | .......................... | D23/366 |
| 2005/0169666 A1 * | 8/2005 | Porchia et al. | ................ | 399/111 |
| 2007/0031298 A1 | 2/2007 | Roumpos et al. | | |

(Continued)

OTHER PUBLICATIONS

Co-pending design U.S. Appl. No. 29/405,477 to John Browder, filed Nov. 2, 2011, titled "Heating Plate."

(Continued)

*Primary Examiner* — Thor Campbell
(74) *Attorney, Agent, or Firm* — Brian Harris

(57) ABSTRACT

A light and fragrance producing device includes an electrically powered light source and a separate electrically powered heating element. The device also includes a fragrance disk that can emit fragrances when heated by the heating element. The fragrance disk also can be configured to remain solid while heated by the heating element rather than melting or evaporating. The device can also include a decorative outer housing that can be interchangeable.

7 Claims, 9 Drawing Sheets

U.S. PATENT DOCUMENTS

| | | | |
|---|---|---|---|
| 2007/0036673 A1* | 2/2007 | Selander | 422/5 |
| 2007/0230197 A1* | 10/2007 | Scannell | 362/418 |
| 2008/0129226 A1* | 6/2008 | DeWitt et al. | 315/307 |
| 2008/0130266 A1* | 6/2008 | DeWitt et al. | 362/96 |
| 2008/0226269 A1 | 9/2008 | DeWitt et al. | |
| 2009/0068068 A1* | 3/2009 | Harris et al. | 422/125 |
| 2010/0025490 A1* | 2/2010 | Bushman et al. | 239/7 |
| 2012/0020052 A1 | 1/2012 | McCavit et al. | |

OTHER PUBLICATIONS

Co-pending design U.S. Appl. No. 29/405,474 to John Browder, filed Nov. 2, 2011, titled "Fragrance Disk."

* cited by examiner

FRAGRANCE PRODUCING LIGHTING DEVICE

RELATED APPLICATIONS

This is a continuation-in-part application of U.S. patent application Ser. No. 13/171,730, filed Jun. 29, 2011, titled "FRAGRANCE PRODUCING LIGHTING DEVICE," which is hereby incorporated herein by reference. This application also claims the benefit of U.S. Provisional Patent Application No. 61/434,185, filed Jan. 19, 2011, titled "FLAMELESS CANDLE WARMERS AND FRAGRANCE DISKS," which is hereby incorporated herein by reference.

BACKGROUND

1. Technical Field

The present disclosure relates generally to electrically-powered lighting devices and, in particular, to an electric lighting device capable of dispersing fragrances through the use of a polymeric disk impregnated with said fragrances that are released into the air surrounding the device during operation.

2. Related Art

Various configurations of electrically-powered fragrance producing lighting devices are known. Typically, such prior devices use various heat sources, such as a tea light or a light bulb, that simultaneously act to emit light and to slowly warm wax-based substances that are heavily scented with a fragrance. The heat sources of such devices act to turn the waxy fragrance-scented substance from an initial solid state over time into a liquid state. The typical configuration of such prior devices requires that a tray containing the waxy substance be placed immediately above the heat/light source so that sufficient heat is applied to said substance. One drawback of the foregoing prior device configuration is that it generally requires the aforementioned tray containing hot wax to be located at the highest point of the device. Such a configuration can potentially be dangerous to persons and pets and damaging to property if the device or an object on which the device rests is bumped forcefully enough such that the tray is partially or completely dislodged, allowing hot wax to be spilt out of the tray.

Another drawback to such prior device configurations is that because the heat source needed to melt the fragrance-producing wax or other substance also acts as a light emitting element, said light emitting element is required to be located in very close proximity to the fragrance producing substance so as to sufficiently warm said substance. This requirement that the light/heating source be in close proximity to the fragrance producing substance severely limits available design configurations of such devices, often leading to design compromises that results in less than optimal displays of lighting from the device.

Another drawback of such prior device configurations utilizing wax type substances, and perhaps one of the least desirable aspects of such devices, is the high level of maintenance required of users of such devices. In particular, when the fragrance contained in the waxy substance is exhausted or the user wants to change the substance so that a different fragrance is produced, the wax is usually melted, poured out and the tray containing the substance is cleaned.

SUMMARY

Fragrance and light producing devices are described herein. According to one aspect of the present disclosure, a device can comprise a base unit having a heating surface and a light source. The device can also comprise a fragrance disk supported by the base unit. The fragrance disk can include a hole, and the heating surface can include a raised surface feature configured to extend into the hole in the fragrance disk.

In some embodiments, the raised surface feature can be one of a plurality of raised surface features on the heating surface. In some such embodiments, the hole can be one of a plurality of holes in the fragrance disk. In some such embodiments, each of the plurality of raised surface features can be configured to extend into one of the holes in the fragrance disk, including embodiments where multiple raised surface features may extend into one of the holes in the fragrance disk. Alternatively, each of the plurality of raised surface features can be configured to extend into respective holes in the fragrance disk.

In some embodiments, the fragrance can disk further include a peripheral outer surface, wherein at least one recess is formed in the peripheral outer surface.

In some embodiments, the light source can comprise a plurality of light emitting diodes, and the base unit can further comprise at least one electric resistive heating element for heating the heating surface.

According to another aspect of the present disclosure, a device can comprise a base unit having a housing, a heating element, and a light source. The device can also comprise a fragrance disk supported by the base unit. At least a portion of an upper surface of the heating element can be in direct contact with the fragrance disk through an opening in the housing.

In some embodiments, the fragrance disk includes a hole, and the heating surface includes a raised surface feature configured to extend into the hole in the fragrance disk. In some such embodiments, the raised surface feature can be one of a plurality of raised surface features on the heating surface. In some such embodiments, the hole can be one of a plurality of holes in the fragrance disk. In some such embodiments, each of the plurality of raised surface features can be configured to extend into one of the holes in the fragrance disk, including embodiments where multiple raised surface features may extend into one of the holes in the fragrance disk. Alternatively, each of the plurality of raised surface features can be configured to extend into respective holes in the fragrance disk.

In some embodiments, the fragrance disk can include a peripheral outer surface, wherein at least one recess is formed in the peripheral outer surface.

In some embodiments, the light source can comprise a plurality of light emitting diodes, and the heating element can comprise at least one electric resistive heating element for heating the upper surface of the heating element.

According to yet another aspect of the present disclosure, a device can comprise a heating element configured to heat to a predetermined peak operating temperature, a fragrance disk configured to emit a fragrance when heated by the heating element, and a light source operable to emit light. The fragrance disk can be configured to remain in solid form while heated by the heating element at the peak operating temperature.

In some embodiments, the fragrance disk can include a hole, and the heating surface can include a raised surface feature configured to extend into the hole in the fragrance disk. In some such embodiments, the raised surface feature can be one of a plurality of raised surface features on the heating surface. In some such embodiments, the hole can be one of a plurality of holes in the fragrance disk. In some such embodiments, each of the plurality of raised surface features can be configured to extend into one of the holes in the fragrance disk, including embodiments where multiple raised surface features may extend into one of the holes in the fragrance disk. Alternatively, each of the plurality of raised surface features can be configured to extend into respective holes in the fragrance disk.

In some embodiments, the fragrance disk can include a peripheral outer surface, wherein at least one recess is formed in the peripheral outer surface.

In some embodiments, the light source can comprise a plurality of light emitting diodes, and the heating element can comprise at least one electric resistive heating element for heating the upper surface of the heating element.

BRIEF DESCRIPTION OF THE DRAWINGS

Features, aspects, and embodiments of the present disclosure are described in conjunction with the attached drawings, in which.

Figure 1:
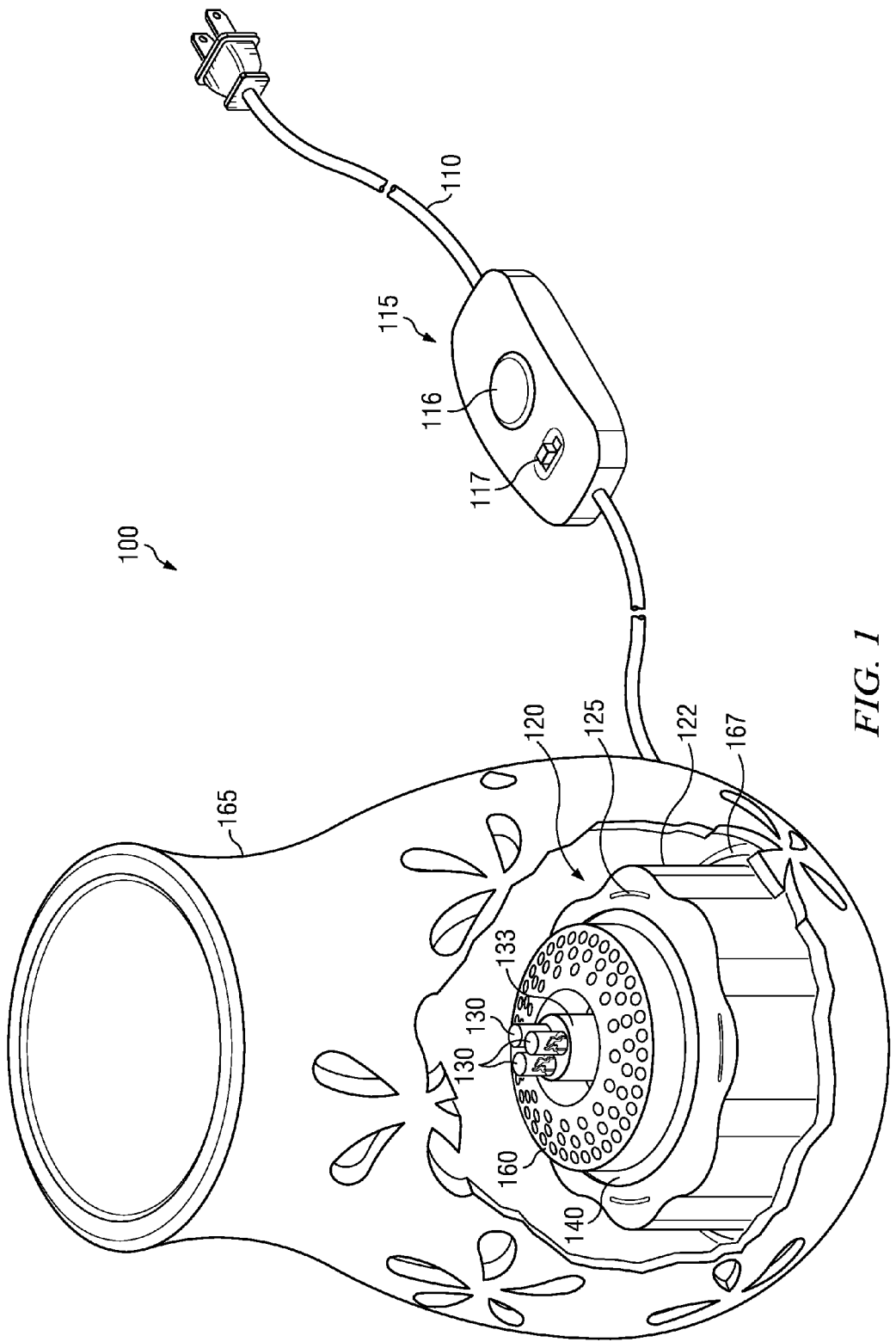
FIG. 1 shows a perspective and cut-away view of an embodiment of the lighting device of the present disclosure.

Where used in the various figures of the drawings, the same reference numerals designate the same or similar parts. Furthermore, when the terms "front," "back," "first," "second," "upper," "lower," "height," "top," "bottom," "outer," "inner," "width," "length," "end," "side," "horizontal," "vertical," and similar terms are used herein, it should be understood that these terms have reference only to the structure shown in the drawing and are utilized only to facilitate describing embodiments of the present disclosure.

All figures are drawn for ease of explanation of the basic teachings of the present disclosure only; the extensions of the figures with respect to number, position, relationship, and dimensions of the parts will either be explained or will be within the skill of persons of ordinary skill in the art after the following teachings of the present disclosure have been read and understood. Further, the exact dimensions and dimensional proportions to conform to specific width, length, and similar requirements will likewise be within the skill of the art after the following teachings of the present disclosure have been read and understood.

Embodiments of the fragrance producing lighting device according to the present disclosure will now be described in detail with reference to the accompanying drawings.

DETAILED DESCRIPTION

Referring to FIG. 1, a perspective view of an embodiment of the fragrance producing lighting device 100 of the present disclosure is shown. References made herein to "fragrance," "fragrant," or other such terms should not be interpreted as being limited to deodorizing or pleasing aromas. For example, in some embodiments, the "fragrance" may be intended as an insect repellant or chosen for medicinal purposes.

The lighting device 100 is electrically powered. In the illustrated embodiment, electrical power can be received via a wired connecting cord 110 suitable for providing for connection of the device to an A/C power source such as a common residential 110 volt or 220 volt outlet (not shown). Although the illustrated embodiment of the device 100 is configured to be connected to an A/C power source, it is contemplated that alternative embodiments may be powered by additional and/or alternative means, for example battery power sources capable of providing the necessary power requirements of the device. Likewise, those of ordinary skill in the art will recognize that other alternative embodiments (such as that which appears in FIG. 6 herein) intended primarily for outdoor use may include configurations of the device that are powered through the utilization of one or more solar cells and rechargeable batteries and may include a post or stake for supporting the device in the ground or other surface.

Figure 2:
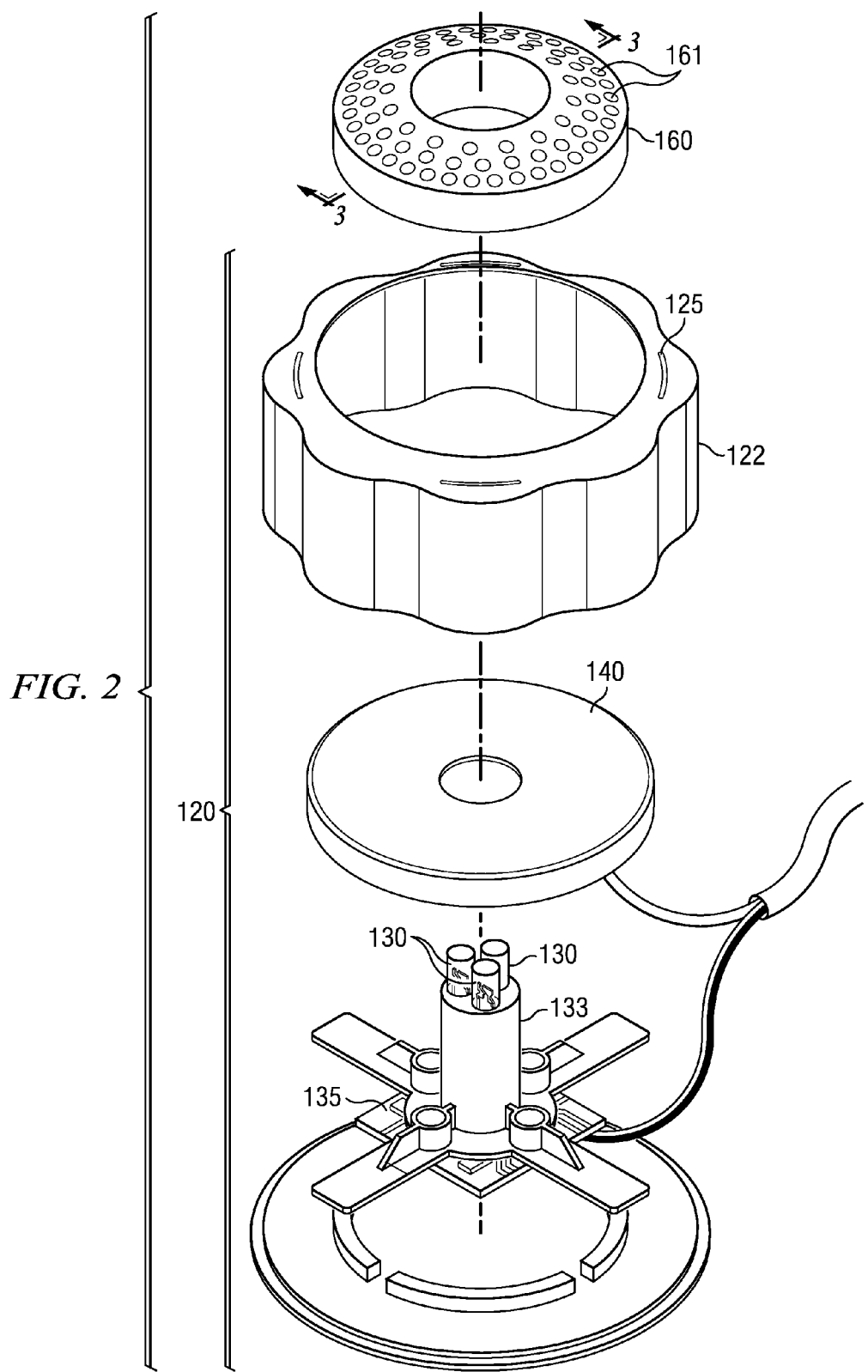
FIG. 2 shows an exploded view of the base unit, light sources, heating element and fragrance disk of the embodiment shown in FIG. 1.

Referring to both FIG. 1 and to FIG. 2, the illustrated embodiment of the device 100 includes a base unit 120 that is connected to the connecting cord 110, a plurality of electric light sources 130, and an electric heating element 140. The housing 122 of the base unit 120, which can be composed primarily of plastic material, serves as a support structure upon which the light sources 130 and heating element 140 may be mounted, as well as a support structure for at least a portion of the circuitry used to deliver power to and control the operation of said light sources 130 and heating element 140. The housing 122 of the base unit 120 may include one or more optional slots 125 or other openings to allow for ventilation of heat produced by the heating element 140. A decorative outer housing 165, discussed in further detail below, surrounds the base unit 120 and includes multiple openings that allow for emission of light from the light sources 130 and dispersal of fragrance from a fragrance disk 160.

The heating element 140 of the present embodiment includes a heating plate of the type generally known in the art, containing resistive elements (not shown) for generating heat and related control system circuitry (not shown) for controlling the heat produced by said resistive elements. Other heating element configurations capable of producing the heat necessary to optimally operate the device will be known and may be successfully utilized by those of ordinary skill in the art. At least a portion of the upper surface of the heating element 140 is exposed through an opening in the housing 122 so that the fragrance disk 160 can be placed directly onto the upper surface of the heating element 140. At least a portion of the upper surface of the heating element 140 is formed of a metal or other material (such as some ceramic materials) suitable for use as a heating surface, particularly a surface suitable for heating to as much as 120° F., 130° F., 150° F., or more depending on the embodiment.

It should be noted that it is not essential for the light sources 130 and heating element 140 to be located in close proximity to one another in the device 100. In fact, alternative embodiments may be configured such that the light source(s) 130 and heating element 140 are located at various distances from one another in the device 100. The potential for such alternative configurations of the positioning of the light source(s) 130 and the heating element 140 is one advantage over prior devices, such as those discussed above, that rely on the transfer of heat from the light sources to the fragrance-emitting component.

Referring back to FIG. 1, some embodiments can include a control unit 115. The function or functions that the control unit 115 is capable of performing and the location of the control unit 115 can vary. Also, in some embodiments, user controls can be located apart from each other rather than located together on a single control unit 115.

In the illustrated embodiment, the control unit 115 is incorporated into the wired connecting cord 110 so as to provide for user control of the various functions of the device such as activation of the heating element and light sources. In the illustrated embodiment, the control unit 115 includes switches 116 and 117.

In some embodiments, the switch 116 can be a push-button power switch that is provided to allow a user to control the delivery of power to the light sources 130, while the switch 117 can be a three position sliding switch 117 configured to control delivery of power to the heating element 140. It should be noted that alternative embodiments may include a unitary switch controlling both the heating element and the light sources.

Alternatively, in some embodiments, one of the switches can be a simple on/off switch, while the other of the two switches can be a timer switch. For example, the switch 116 can be a push-button power switch that is provided to allow a user to simultaneously control the delivery of power to the light sources 130 and to the heating element 140. The switch 117 can be a push-button power switch that activates a timer mode of operation.

For example, in some embodiments, the timer mode of operation can be configured such that the lighting elements 130 and heating element 140 are turned on (receive electrical power) for a first predetermined period of time, after which the lighting elements 130 and heating element 140 are automatically turned off (disconnected from electrical power).

In some such embodiments, after expiration of the first predetermined period of time during which the lighting elements 130 and heating element 140 are turned on, the lighting elements 130 and heating element 140 are automatically turned off for a second predetermined period of time, after which the lighting elements 130 and heating element 140 are automatically turned back on for the first predetermined period of time, and this cycle can continue until interrupted by the user and/or if operation is otherwise interrupted, e.g., due to unexpected loss of a power source.

For example, in some embodiments, the timer mode can be configured such that the first predetermined period of time is five hours and the second predetermined period of time is nineteen hours. Other time periods can be used. But in embodiments where the first time period is five hours and the second time period is nineteen hours, once the timer mode is activated by the user, the lighting elements 130 and heating element 140 are automatically turned on at approximately the same time every day, and five hours later are automatically turned off at approximately the same time every day.

In addition to simply being convenient for a user not wanting to unnecessarily waste power, the foregoing timer functionality can act as a safety feature for preventing inadvertently prolonged periods of heating-element operation.

As another example, in some embodiments, the switch 117 can be a three position switch for controlling the heating element 140 and/or lighting devices 130 where the three switch positions respectively correspond to on, off, and a timer position. In such embodiments, the timer position can activate a timer mode as described above.

Light Sources

Referring again to both FIG. 1 and FIG. 2, the present embodiment has multiple light sources and in particular, three light emitting diodes (LEDs) 130. The LEDs 130 are electrically connected to circuitry 135 housed within the base unit 120, which is in turn electrically connected to a power and control circuit housed in the control unit 115 as shown in FIG. 1. The circuitry includes a printed circuit board (PCB) 135 which is connected to the control unit and the LEDs. Although the present embodiment includes three LEDs, it should be noted that alternative embodiments of the device may include a greater (more than three) or lesser (one or two) number of LEDs or other light sources depending on a number of factors including, but not limited to, the intensity of the light output desired, the power requirements of said light sources, manufacturing costs and the size of the light sources. Moreover, alternative embodiments may include one or more light sources illuminating at constant intensity.

Fragrance Disk

Still referring to FIG. 1 and FIG. 2, a fragrance disk 160 rests on the upper surface of the heating element 140 during operation of the device 100. The fragrance disk 160 is the source of the fragrance produced by the device 100 and is replaceable by the user. The fragrance disk 100 of the present embodiment is annular in shape, having a circular aperture formed in the central portion of the disk 160 and a plurality of venting holes formed in the annular region of said disk 160. It should be noted that for the purposes of the teachings and claims herein, the term "disk" shall not be construed so as to be limited to circular or annular shaped forms but may also include any number of various other non-circular polygonal shapes. Alternative embodiments of the fragrance disk 160 are possible that include various differences, for example variations in overall shape, number of holes, size of holes, and/or shapes of the holes. Such alternative embodiments can include alternative embodiments of the fragrance disk 160 that are discussed below.

The fragrance disk 160 can be at least partially composed of a polymeric material, for example ethylene vinyl acetate (EVA), which is a known copolymer of ethylene and vinyl acetate that is flexible and remains in a substantially solid state when heated by the heating element 160. The EVA disk 160 can be configured so as to not substantially deform at temperatures of less than two hundred degrees Fahrenheit, although some shrinkage of the disk can occur over time as the vaporizing agents are dispersed into the air.

As those with skill in the art will appreciate, the properties of EVA allow it to be impregnated, embedded, or absorbed in or infused with (collectively referred to herein by use of the term "impregnate" or variations thereof) various vaporizing agents such as, for example, a fragrance, permitting it to be used as a fragrance reservoir in the device. It should be noted that for the purposes of this specification and the claims recited herein, the term "vaporizing agent" should be construed to mean any substance that may exist in a substantially solid and or liquid state but that is also capable of existing in a substantially vaporized and/or aerosolized state when heated.

Methods for making and using EVA and other polymeric materials and impregnating them with vaporizing agents such as fragrances, which can include odor-neutralizing substances, insecticides and substances having medicinal properties that are known in the art. EVA material of the fragrance disk 160 can have a molecular weight in the range of 10,000 Daltons to 100,000 Daltons. Vaporizing agents may be impregnated into the EVA fragrance disk 160 at weight percents varying from 10 to 90%, from 20 to 80%, from 30 to 70%, from 30 to 60%, and from 30 to 50%. For example, in some embodiments, the fragrance disk can be composed of about 75% EVA by weight and about 25% of fragranced vaporizing agent by weight. It should be noted however, that alternative embodiments of the fragrance disk 160 may include other combinations by weight of the polymeric material and the vaporizing agent.

Alternative embodiments of the fragrance disk 160 may be composed of other polymeric materials including, but not limited to, polyethylene (high or low density), polypropylene, polyvinyl chloride, polystyrene, polycarbonate, acrylonitrile butadiene styrene (ABS), PEBAX and polymethylpentene, ethyl vinyl alcohol, polystyrene, acrylic polymers, polycarbonates, polyurethanes, and nylons.

Possible fragrances to be impregnated in the fragrance disk 160 may be selected from the non-exhaustive list of fragrances including musk oil, civet, castreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, cauout oil, salvia oil, clove oil, chamomile oil, costus oil, labdanum oil, broom extract, carrot seed extract, jasmine extract, minmosa extract, narcissus extract, olibanum extract, rose extract, acetophenonene, dimethylinadane derivatives, naphthaline derivatives, allyl caprate, alpha-amylcinnamic aldehyde, anethole, anisaldehyde, benzyl acetate, benzyl alcohol, benzyl propionate, borneol, cinnmayl acetate, cinnamyl alcohol, citral citronellal, cumin aldehyde, cyclamen aldehyde, decanol, ethyl butyrate, ethyl caprate, ethyl cinnamate, ethyl vanillin, eugenol, geraniol, exenol, alpha-hexylcinnamic aldehyde, hydroxycitrolnellal, indole, iso-amyl acetate, iso amyl isovaleratek iso-eugenol, linalol, linalyl acetate, p-methylacetophenone, methyl anthranilate, methyl dihydroasmonate, methyl eugenol, methyl-beta-naphthol ketone, methylphenhlcarbinyl acetate, musk ketol, mustk xylol, 2,5, 6nanodinol, gannna-nanolactone, phenylacetoaldehydrodimethyl acetate, beta-phenylethyl alcohol, 3,3,5trimethylcyclohexanol, gamma-undecalactone, undecenal, vanillin, and mixtures thereof. The foregoing hindered amines may be added to the fragranced vaporizing agent at weights of between 0.1% and 2.0% by weight of the EVA, preferably at 0.7% by weight. Those of skill in the art will recognize that in constructing the fragrance disk, it is also desirable to mix the fragrance with hindered amines such as for example, 1-(2-hydroxy-2-methylpropoxy)-4-octadecanoyloxy-2,2,6,6-tetramethylpiperidine; 1-(2-hydroxy-2-methylpropoxy)-4-hydroxy-2,2,6,6-tetramethylpiperidine; and bis(1-octyloxy-2,2,6,6-tetramethylpiperidin-4-yl)sebacate. Further, various antioxidants such as tertiary butylhydroquinone, butylated hydroxyanisole, phenol bisphosphite, and butylated hydroxytoluene are preferably added to the fragranced vaporizing agent at amounts of between 0.015% and 2.5% by weight of the EVA or other polymer, and preferably between 0.2% and 0.5% by weight.

It is contemplated that in alternative embodiments the EVA material used in the fragrance disk 160 may also be impregnated with other vaporizing agents such as an insecticide. The insecticide may be selected from the non-exhaustive list of substances including citronella, pyrethrum, methyl bromide, aluminum phosphide, and magnesium phosphide. Other alternative embodiments may also utilize a disk 160 impregnated with vaporizing agents having medicinal properties. Such vaporizing agents having medicinal properties may be selected from the non-exhaustive list of preparations including eucalyptus oil, menthol, camphor, thymol, turpentine oil, 1-desoxyephedrine, and bornyl acetate. In other alternative embodiments, the foregoing substances may be impregnated in the disk in combination with one or more other fragrances or alone. In other words, it is contemplated that alternative embodiments of the disk 160 as disclosed and claimed herein, may or may not be impregnated with fragrances, which can include one or more vaporizing agents not chosen primarily for the production of a pleasing aroma.

The beneficial properties of the EVA material used in the disk 160 provide for the distribution of heat necessary to permit an approximately uniform heating effect throughout said disk 160. When properly heated, the configuration of the disk 160 allows warm air via convection to lift fragrant vaporizing agents from the disk 160 into the ambient air. To facilitate this aspect of dispersal, a plurality of smaller (smaller than the central aperture) holes 161 are placed throughout the annular region (region constituting disk) of said disk 161 to accommodate the effect of convection.

Figure 3:
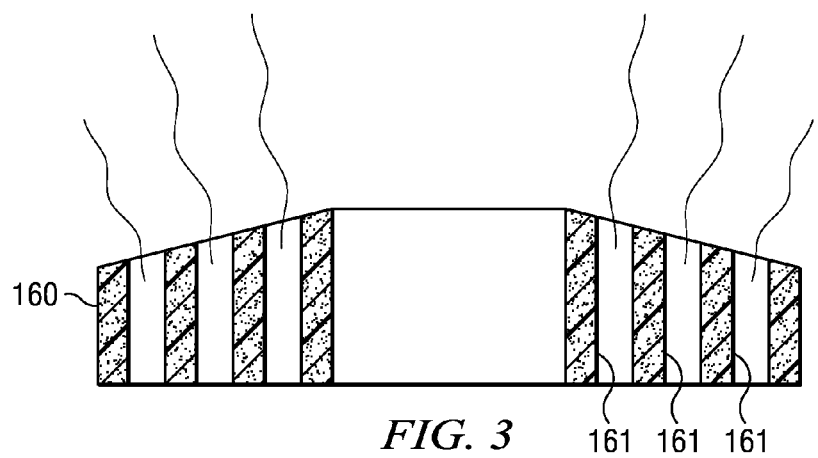
FIG. 3 shows a cross-sectional view of the fragrance disk shown in FIG. 2, along Line 3 therein.

FIG. 3 shows a cross-sectional view of the fragrance disk 160 taken along section lines 3-3 in FIG. 2. As shown in FIG. 3, a plurality of venting holes 161 can be formed in the disk 160. The venting holes 161 can be substantially cylindrical in form and extend completely through the disk 160, i.e., from the bottom of said disk 160 to the top of said disk 160. Alternatively, it is contemplated that the holes 161 can have any of a variety of alternative shapes, including rectangular, cones, slots, etc, for example as described below in connection with FIGS. 9-11. Greater numbers of venting holes can allow for a higher exposed surface of the disk and, thus, increased rates of vaporizing-agent dispersal into the air.

During operation of the present embodiment of the device 100, the upper surface of the heating element 140 can heat from room temperature to a temperature in a range of approximately 100° F. (degrees Fahrenheit) to approximately 150° F. For example, in some embodiments, the upper surface of the heating element 140 can heat from room temperature to a temperature in a range of approximately 110° F. to approximately 135° F. In some such embodiments, the upper surface of the heating element 140 can heat from room temperature to a temperature in a range of approximately 118° F. to approximately 126° F., such as, for example, approximately 122° F. In some embodiments, as discussed in greater detail elsewhere herein, the power provided to the heating element 140 can vary during operation, so temperature of the upper surface of the heating element 140 can fluctuate during operation between room temperature and a peak temperature, such as a temperature in a range of approximately 100° F. to approximately 150° F., or in a range of approximately 110° F. to approximately 135° F., or in a range of approximately 118° F. to approximately 126° F., such as, for example, approximately 122° F. As will be recognized by those of skill in the art, other temperature ranges may be used depending on such factors as the density of the polymeric material of the fragrance disk, the properties of the vaporizing agent impregnated into the disk, the desired rate of dispersal of the vaporizing agent, power requirements, and composition and proximity of potentially heat-sensitive components such as the base unit housing and light sources. It should be note that heating of the EVA-composed fragrance disk of the present embodiment will cause said disk to reduce in size (referred to as "shrinkage" above) as the impregnated vaporizing agent(s) are dispersed.

Referring to FIG. 1 and FIG. 2, a post 133 is provided for supporting the light sources 130. The post 133 can be positioned at or near the center of the annular heating element 140, or elsewhere. The light sources 130 can be LEDs or other light elements that are not a significant source of heat for heating the disk 160. That is, the light sources 130 can be provided primarily for illumination purposes and serve no significant role in heating the disk 160. The post 133 can position the height of the light sources 130 for desired lighting intensity relative to the specific decorative housing 165 that is being used. In addition, the decorative outer housing 165 can be interchangeable with one or more other decorative outer housings, and in some embodiments the light sources 130 can be repositionable by the user to direct light as desired based the design of the decorative housing 165. Alternative embodiments may be configured such that the circuitry controlling the light sources 130 can be placed in close proximity to the light sources 130 (for example, at the top of the post 133) or within the heating element housing 122 (for example, below the post 133).

Figure 4:
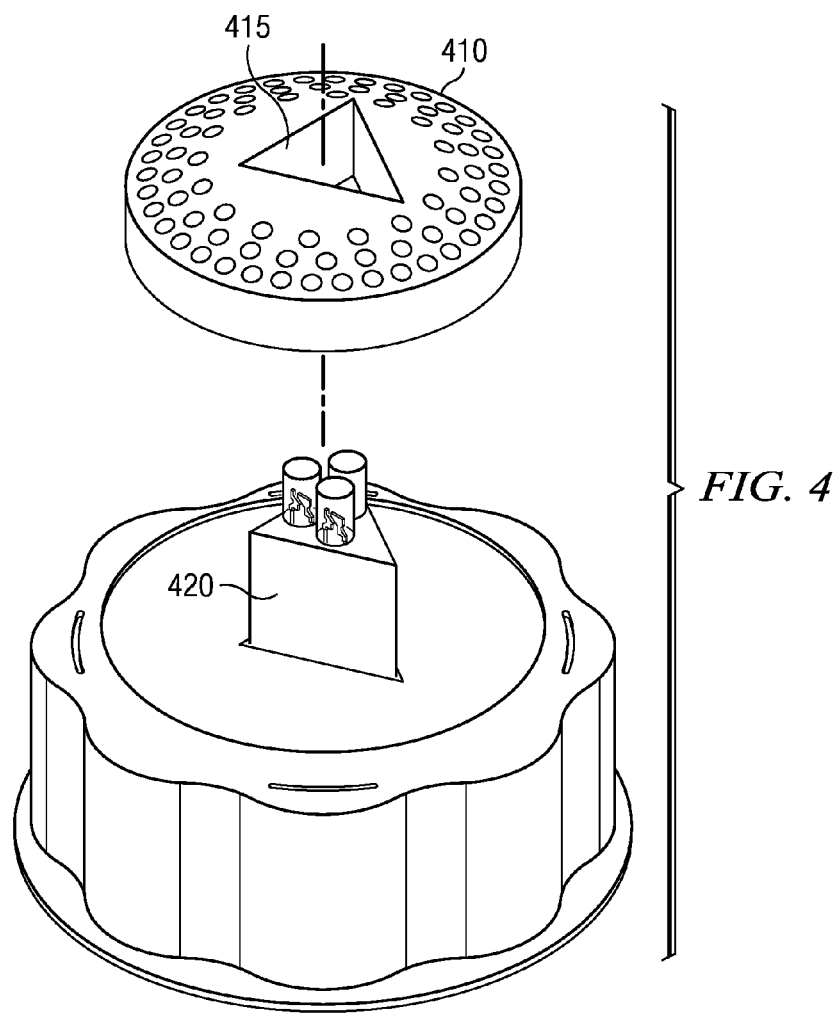
FIG. 4 shows perspective view of an alternative embodiment of the base unit post and fragrance disk of the present disclosure.

Referring now to FIG. 4, some embodiments of the device 100 can include an alternative fragrance disk 160, referred to as alternative fragrance disk 410, and an alternative post 133, referred to as post 420. Desirable operation of the device 100 is likely to occur when the particular composition of the fragrance disk is well-matched with the operating temperature range of the heating element. If fragrance disks not well-suited for use with the heating element of a particular embodiment of the device are used in combination, it is possible that less than desirable results will occur.

Accordingly, in some embodiments of the lighting device such as that shown in FIG. 4, the post can be shaped so as to mate with fragrance disks that are well-suited for the operating temperature range of the device's heating element. For example, the cross-sectional shape of the post can be selected so as to also encourage the use of fragrance disks having correspondingly-shaped central apertures. For example, referring specifically to the embodiment shown in FIG. 4, a device 100 having heating element 140 operating within a certain temperature range that is well-suited for fragrance disk 410, the device 100 can have the post 420 having a triangular cross-section that mates with the triangular central aperture 415 of the fragrance disk 410. Alternative cross-sectional shapes and/or other mating features can be used. Thus, a user can easily determine whether they are using an appropriate fragrance disk by matching easily-discernable features of the device and the disk. A user having a fragrance disk that appears to be intended for use with a particular lighting device, e.g., having a central aperture shaped in a manner corresponding to the cross-sectional shape of the post of said device, can install said disk for operation. Ideally, the foregoing alternative configuration will promote the combined use of fragrance disks intended for use in conjunction with particular lighting devices.

Other Outer Housing Configurations

Figure 5:
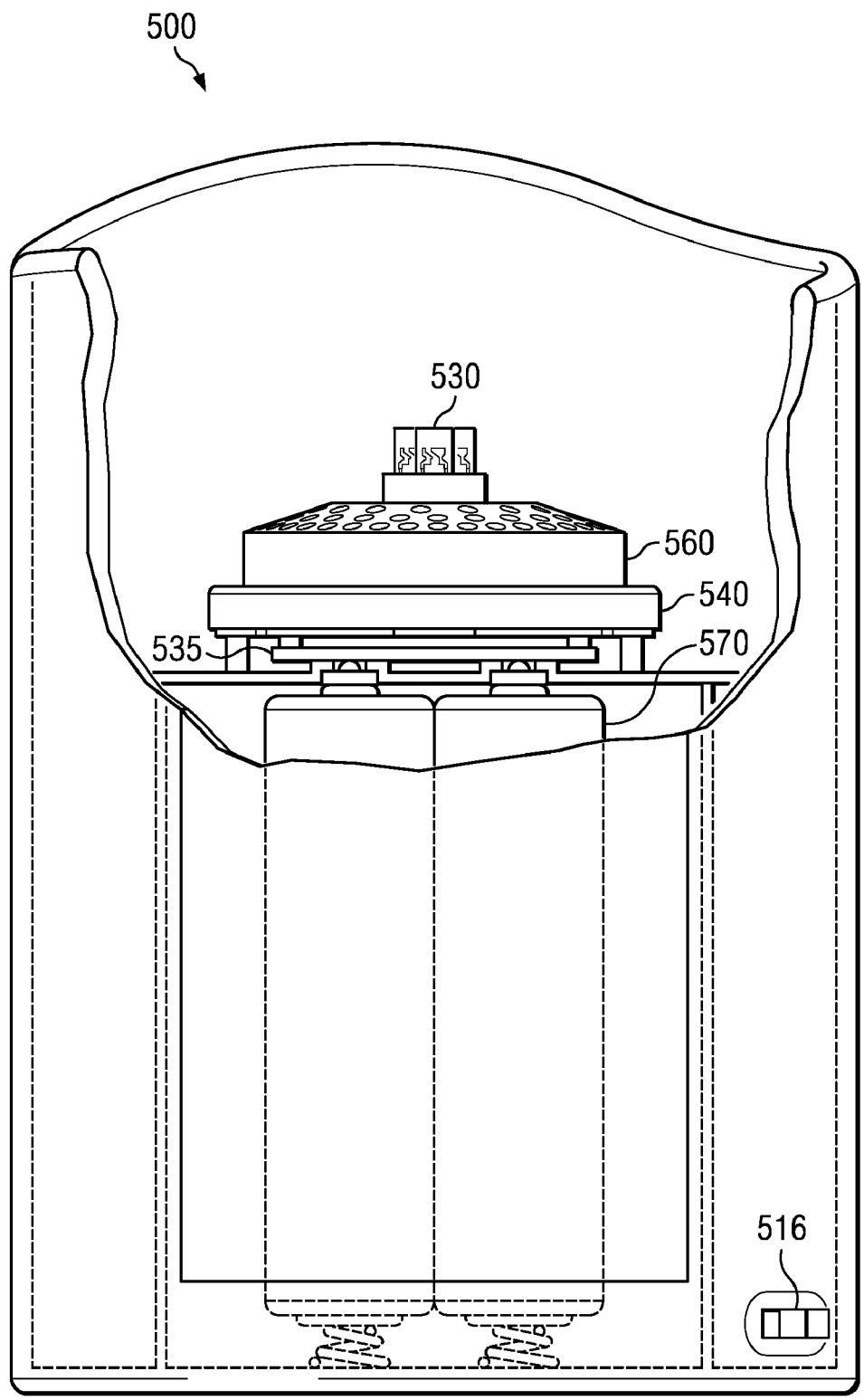
FIG. 5 shows a side cut-away view of an alternative embodiment of the lighting device of the present disclosure.

In general, a wide variety of outer housing configurations can be used with the device 100. For example, FIG. 5 shows a side cut-away view of an alternative embodiment of the disclosed lighting device 100, the alternative embodiment being generally designated as lighting device 500, where a candle-like structure serves as a decorative outer housing and support for the base unit and other components of the device. In the alternative embodiment shown at FIG. 5, a cavity is formed in the upper portion of the candle-like housing so as to resemble a genuine candle that has been used. The upper rim of the candle-like housing is also curved to provide the appearance of a genuine candle. Mounted onto the floor of the candle-like housing cavity are the heating element 540, light sources 530, and the power and control circuitry 535 for operating said light sources and said heating element. The fragrance disk used in this alternative embodiment is annular in shape, allowing it to be removably inserted over the light sources and post to rest on the upper surface of the heating element in the same manner as shown in the embodiment appearing at FIG. 1 and FIG. 2.

Still referring to the alternative embodiment shown at FIG. 5, the illustrated embodiment of the device 500 is battery powered. However, other power sources can be used. A battery enclosure is formed in the lower portion of the candle-like housing, below the aforementioned floor of the cavity of said housing. Removable batteries 570 mounted within the battery enclosure are electrically connected to the power and control circuitry 535, which is in turn connected to the heating element 540 and light sources 530. It is contemplated that various types of batteries may be utilized to provide power to alternative embodiments, including but not limited to, alkaline, lithium, nickel-cadmium, nickel-metal hydride, rechargeable, and non-rechargeable batteries. A switch 516 mounted on the candle housing and connected (not shown) to the circuit allows for control of the operation of the heating element and light sources by users of the device. Other user-operated control unit configurations having one or more switches and timers may be integrated into the device or remotely connected, wired or wirelessly, to the device in some embodiments.

Those of ordinary skill in the art will recognize that other various alternative embodiments of the outer housing can be used to enclose and support the other components of the device. For example, luminary type outer housings may be used to provide innumerable décor oriented designs. Such designs may include an opening at the top of the housing, thus providing a unique visual difference in view of prior art fragrance warmers which are configured such that a melting tray is positioned at the top of the device. Materials used to make the decorative outer housing may include wax, plastic, metal, glass, ceramic, and a combination of these or other materials depending on the nature of the decorative housing used.

Also, in some embodiments, the device 100 can be configured to allow for interchangeable outer housings 165 so that the same inner components, e.g., base unit 120, heating element 140, housing 122, post 133, light sources 130, and fragrance disk 160, can be used with one or more different housings 165. Such embodiments allow the user to change the outer appearance of the device 100 without replacing the entire device 100. In some such embodiments, the decorative housing can be configured to attach to the base unit 120 via a variety of methods including a threaded interface (e.g., screw-on or twist-on), bayonet lug and slot, or press-fit detents, among others. As shown in the embodiment in FIG. 1, it is also possible that the decorative outer housing may simply be provided with a lower opening 167 through the bottom thereof that is large enough to allow the outer housing to be removably set over and about the base unit 120 with no interface or attaching fasteners needed. In other words, the inside diameter of the lower opening 167 can be larger than the largest outside diameter of the base unit 120. The ability to encase the base unit housing in some form of decorative housing improves overall safety of the device as it will isolate the heating portions of the unit to minimize the chance of incidental scalding or burning due to contact with any hot components. However, where the outer housing encases the base unit, the outer housing will preferably include one or more holes there-through to allow for light and/or fragrance to emanate from within the housing (i.e., from the light sources and fragrance disk) to outside of the housing.

Figure 6:
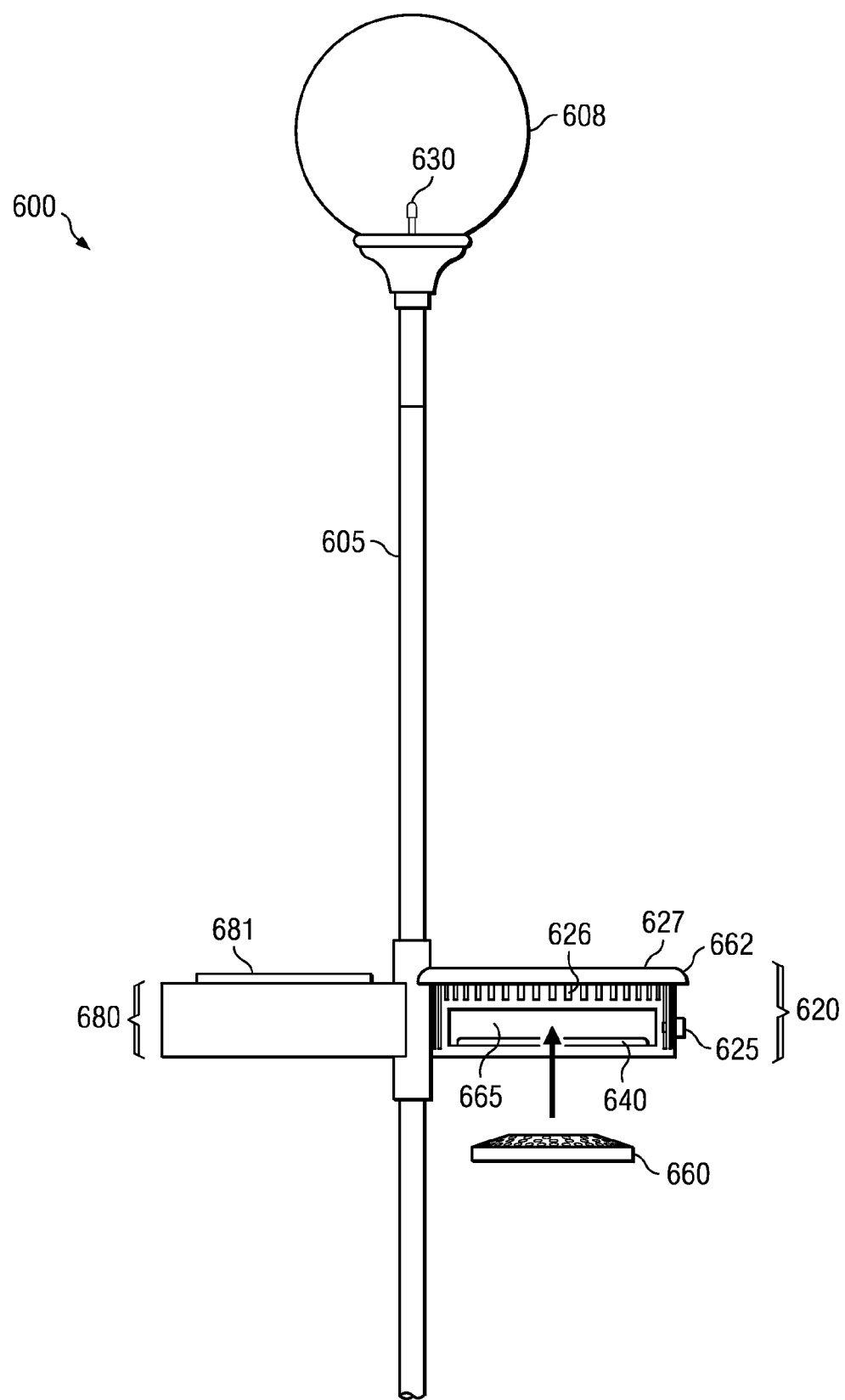
FIG. 6 shows a side view of a further alternative embodiment of the lighting device of the present disclosure.

Referring now to FIG. 6, a side view of an alternative embodiment of the lighting device 100, generally referred to as lighting device 600, is shown. The lighting device 600 can be a garden light that can be used in outdoor environments. The illustrated embodiment of the lighting device 600 includes one or more solar cells 681 for allowing the lighting device 600 to be a solar-powered device, however additional and/or alternative power sources can be used.

The lighting device 600 includes a tubular body 605 upon which is mounted a lens 608. For the purposes of this specification and the claims recited herein, the term "body" should be construed to broadly include any structure upon which the components of the lighting device discussed herein may be mounted. Also for the purposes of this specification and the claims recited herein, the term "lens" should be construed to include any transparent or translucent material through which light may be transmitted.

The lens 608 can be formed of any desired material, including, for example, glass and/or plastic. Also, in some embodiments, the lens 608 can include multiple layers of material. For example, the lens 608 can include an inner plastic layer and an outer glass layer, or vice-versa. In such embodiments, any one or more of the layers can be full or partial layers. For example, a mosaic embodiment of the lens 608 can include one or more layers of material that form a mosaic pattern and that are supported by another layer.

Light source 630 is mounted on the top of said tubular body 605 and within a cavity formed by the lens 608 so as to provide illumination when power is supplied. The light source 630 can include one or more lighting elements, e.g., one or more LEDs. A power unit 680 is supported by the body 605, and the solar cell 681 is supported by the power unit 680. One or more rechargeable batteries (not shown) are mounted within the power unit 680 and are connected so as to be rechargeable by the solar cell 681. The rechargeable batteries can be included as part of a power and control circuit adapted for use in conjunction with the solar cell 681, allowing for the recharging of the rechargeable batteries when the solar cell 681 is exposed to light.

The power unit 680 can be electrically connected to the LED 630 and can supply said LED 630 with power stored in the rechargeable batteries. As is known in the art, the solar cell 681 acts to charge the rechargeable batteries during the daytime when the solar cell is exposed to light. During the nighttime hours, the batteries can supply power to the LED 630 to provide illumination. In some embodiments, a light sensitive switch (not shown), such as known switches that incorporate a cadmium sulfide (CDS) photoresistor, can be used to sense ambient light levels such that the aforementioned circuitry causes the LED 630 to illuminate in the presence of low ambient light levels.

Still referring to FIG. 6, a base unit 620 is also mounted onto the body 605. The base unit 620 supports a heating element 640, which can be mounted on or within the base unit 620. The base unit 620 can be electrically connected to the power unit 680 such that the rechargeable batteries mounted therein can supply the power necessary to operate the heating element 640. Alternatively, a separate power source can be used for the heating element in some embodiments.

In embodiments such as the illustrated embodiment where the heating element is located within the base unit 620, a slot 665 or the like can be provided for allowing access to the heating element 640 such that a user can insert and remove replaceable fragrance disks 660 to and from the heating element 640. In some embodiments, a depressible user-operated ejection button 625 can be provided, e.g., mounted onto the base unit 620. The ejection button 625 can be configured to apply force to the fragrance disk 660 to eject it from the base unit 620. In further alternative embodiments, the user-operated ejection button 625 may work in conjunction with a spring-loaded lever to eject the disk 660.

Slots 626 can be formed on the upper portion of the base unit 620 to allow for ventilation of fragrances into the surrounding air as the fragrance disk 660 is heated by the heating element 640. The fragrances can include any of a variety of vaporizing agents as discussed elsewhere herein, including insecticides.

In some embodiments, an overhang 662 can be formed on the top side of the base unit 620 to prevent rain or other water from entering said base unit 620 when the device is placed outdoors. A spike (not shown), mounting plate, or other support structure can be provided at the bottom of the body 605 to facilitate installation of said body 605, e.g., insertion of said body 605 into the ground or for mounting or placing said body 605 onto a wood or concrete surface for outdoor use. Further, one or more switches (not shown) for controlling the light sources and/or heating element may be implemented in solar-powered alternative embodiments in the manner discussed herein with respect to the various disclosed embodiments.

Power and Control Circuits

A variety of power and control circuits can be used with the disclosed lighting device, for example depending on the type of power source, number of power sources, whether separate controls for the heating element and light sources is desired, and/or whether a timer is desired.

Figure 7A:
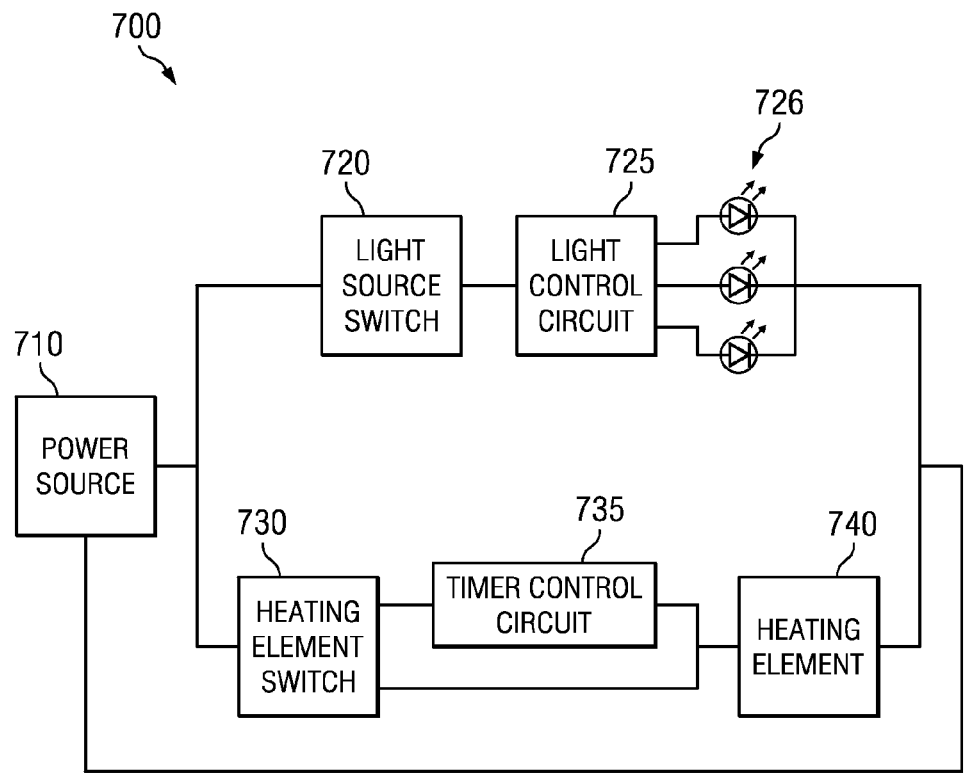
FIGS. 7A and 7B show block diagrams representing respective embodiments of the electrical power and control circuit that can be used in some embodiments of the present disclosure.

FIG. 7A shows a general block diagram of an embodiment of a power and control circuit where separate respective switches are provided for the light source and for the heating element. A power source 710 provides the power for operation of light sources 726 and a heating element 740. While the light sources 726 are shown in FIG. 7A as three LEDs, alternative types and/or numbers of light-producing elements can be used. The power source 710 can be, for example, an A/C power source connected to the control unit 115 shown in FIG. 1. Alternatively, the power source can be a DC power source, such as one or more batteries.

A light source switch 720, for example corresponding to switch 116, is configured to control the delivery of power to a light control circuit 725. The light control circuit 725 can include known light driver circuitry for controlling operation of the light sources 726. The light source 726 can include one or more light-producing elements, for example one or more LEDs.

In some embodiments, the light control circuit 725 can be configured to drive the light sources 726 so as to produce a flickering effect that simulates a candle flame. In such embodiments, the light control circuit 725 can include an integrated circuit and/or other components for intermittently illuminating the light sources 726 to produce a flickering flame-like effect or for driving the light source to produce a substantially constant amount of light. Various circuit configurations and methods for intermittently illuminating one or more light sources are generally known in the art. The means for producing a flickering light in light-producing elements can include pulse width modulation (PWM) techniques via a controller that sets the duty cycle for each light-producing element. Altering the duty cycles of the current supplied to the light-producing elements at high frequencies will achieve a flickering flame-like illumination. One example of the use of PWM techniques to produce a flickering effect is taught by U.S. Pat. No. 7,850,327 to Campbell et al., which is incorporated by reference herein. Alternative means for producing a flickering effect may be accomplished by the use of a controller to otherwise adjust how current is supplied to the light-producing elements. For example, other configurations and methods for delivering power intermittently to light-producing elements to produce a flame-like flickering effect are taught in U.S. Pat. No. 6,719,443 to Gutstein et al., also incorporated by reference herein.

Still referring to FIG. 7A, a heating element switch 730, for example corresponding to switch 117, provides for user control of the heating element 740. Also, in this embodiment a timer control circuit 735 is connected to the heating element switch 730 and includes circuitry for activating and/or deactivating the heating element 740 for pre-determined periods of time as discussed above. Alternatively, the heating element switch 730 may also be used to directly control power to the heating element 740 without any timing functionality.

Figure 7B:
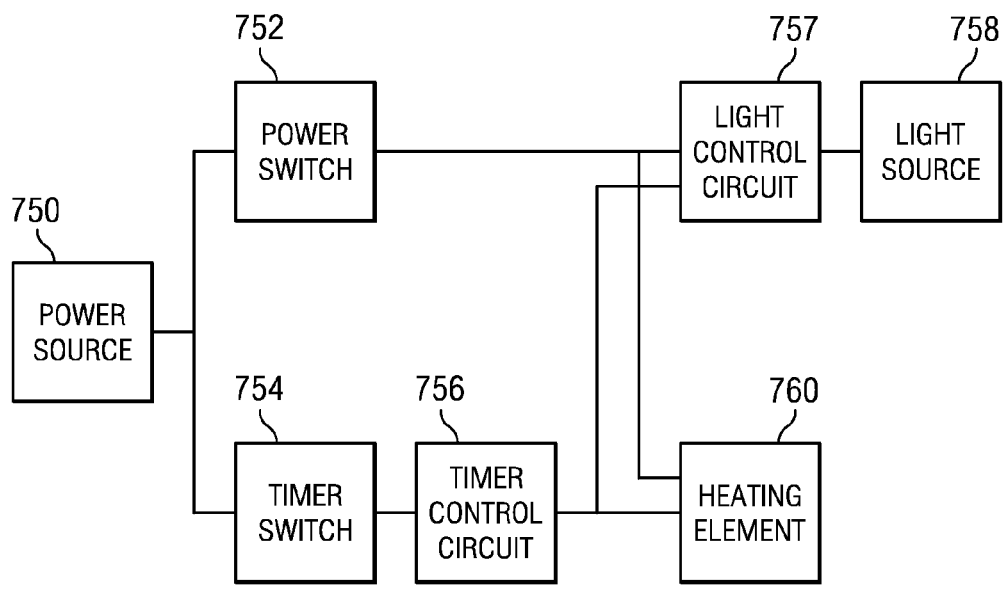

FIG. 7B shows a general block diagram of an alternative embodiment of a power and control circuit where a power switch is provided for controlling both the light source and the heating element. A power source 750 provides the power for operation of the light source 758 and heating element 760. The light source 758 can include one or more light-producing elements, and the heating element 760 can include one or more heat-producing elements. The power source 750 can be, for example, an A/C power source connected to the control unit 115 shown in FIG. 1. Alternatively, the power source can be a DC power source, such as one or more batteries.

A power switch 752, for example corresponding to switch 116, is configured to control the delivery of power to a light control circuit 757 and to the heating element 760. The light control circuit 757 can include known light driver circuitry for controlling operation of the light source 758.

In some embodiments, the light control circuit 757 can be configured to drive the light source 758 so as to produce a flickering effect that simulates a candle flame according to the same methods discussed above in connection with light control circuit 725.

Still referring to FIG. 7B, the timer switch 754, for example corresponding to switch 117, allows a user to activate timer mode of operation, for example as discussed above in connection with FIG. 1. The timer switch 754 is connected to a timer control circuit 735, which includes circuitry for activating and/or deactivating the light source 758 and heating element 760 for pre-determined periods of time as discussed above.

In some embodiments, methods and corresponding circuitry can be used for activating the heating element and/or a fan intermittently to improve the dispersal of the fragrance. For example, in some embodiments, such methods can include varying the amount of electrical power that is provided to the heating element while the heating element is in operation. In some such embodiments, for example, while the heating element is "operational," the power to the heating element can be cycled on and off for predetermined periods of time, e.g., repetitions of ten minute cycles that each includes five minutes on and five minutes off. Methods of cycling the power to the heating element and/or fan from an "on" state to an "off" state (and vice-versa) for pre-determined periods of time can include cycling methods that are known in the art as a means for maximizing the dispersal of fragrance and to aid in conserving power.

In some embodiments, the power cycling of the heating element can be configured such that power is not being actively supplied to the heating element during an "off" state of the cycle and, as a result, the temperature of the upper surface of said heating element cools. Further, during the period in which the heating element is in an "off" state, fragrance that has not yet been dispersed builds up, generally referred to as "head space" in the art. Following the aforesaid "off" state, the aforementioned power and control circuit can act to again supply power to the heating element, causing said heating element to be in an "on" state and, consequently, also causing the upper surface of said heating element to increase in temperature. As the temperature increases, an increased amount of fragrance is dispersed from the disk as a result of the buildup of fragrance during the "off" state of the cycle.

It should be noted that the time periods of the "on" states and "off" states of the heating element cycle can vary from embodiment to embodiment. Also, in some embodiments, the time periods for the "on" and "off" states can differ from each other, e.g., the "on" state can be set for a period of approximately one minute, followed by an "off" state of approximately four minutes. Alternatively, in some embodiments, the time periods for the "on" and "off" states can be approximately the same, e.g., the "on" state can be set for a period of approximately five minutes, followed by an "off" state of approximately five minutes. Similar timing periods may also be employed when the aforementioned power cycling techniques are implemented in connection with embodiments of the device utilizing a fan for the dispersal of fragrance as discussed below.

Figure 8:
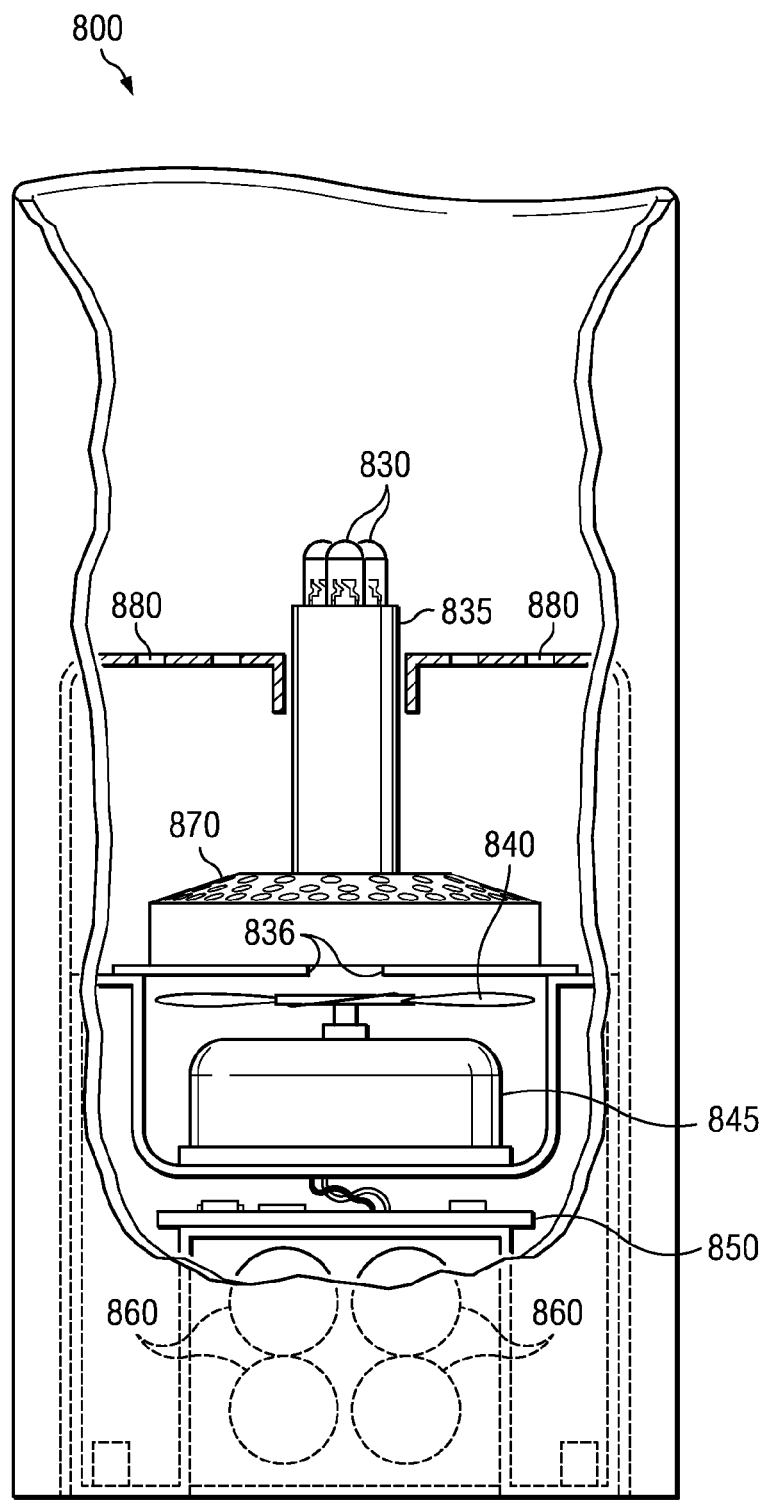
FIG. 8 shows a side and cut-away view of an alternative embodiment of the present disclosure utilizing a fan for fragrance dispersal.

Referring now to FIG. 8, which shows a side and cut-away view of an alternative embodiment 800, a fan is mounted on a lower portion of a battery powered configuration of the device having a candle-like outer housing structure. LEDs 830 mounted on a post 835 are supported in the upper portion of the housing structure. A fragrance disk rests on support legs of the post 835. Below the fragrance disk is a fan comprising fan blades 840 and a battery powered motor 845 configured to rotate said fan blades. A power and control circuit 850 mounted below the fan motor 845 controls the operation of the LEDs 830 and the fan. During operation of the fan motor 845, the fan blades force air upwards through venting holes (as described above) formed in the fragrance disk, causing fragrance to disperse into the ambient air. Those of ordinary skill in the art will appreciate that although the alternative embodiment shown in FIG. 8 does not include a heating element, other alternative embodiments may utilize a heating element in conjunction with a fan, said heating element being mountable just below the fragrance disk.

Figure 9:
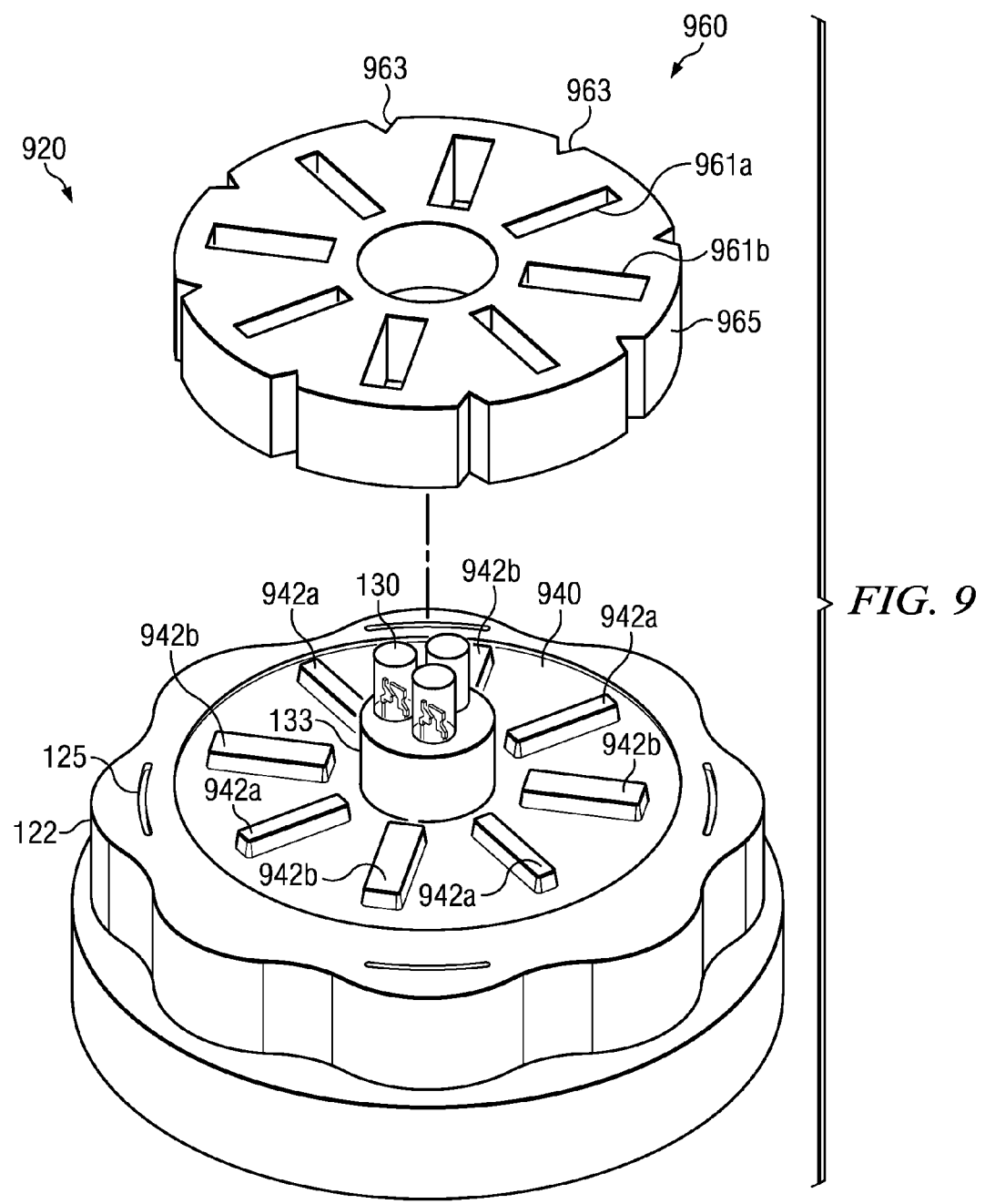
FIG. 9 shows an exploded perspective view of an alternative embodiment of a base unit and an alternative embodiment of a fragrance disk.
Figure 10:
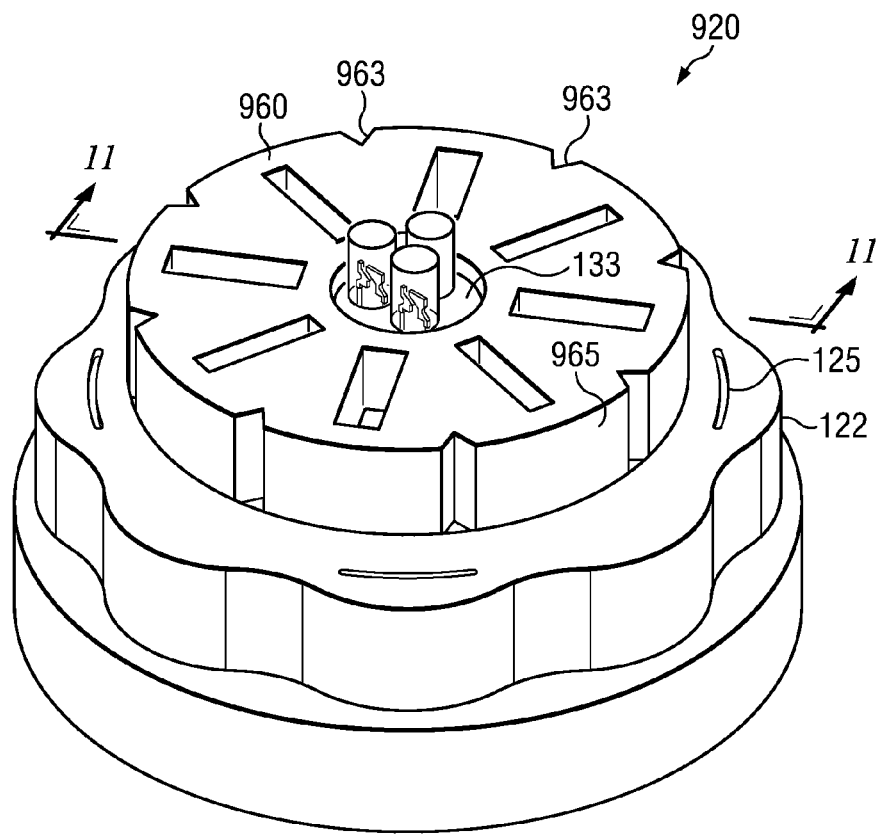
FIG. 10 shows a perspective assembled view of the base unit and fragrance disk shown in FIG. 9.
Figure 11:
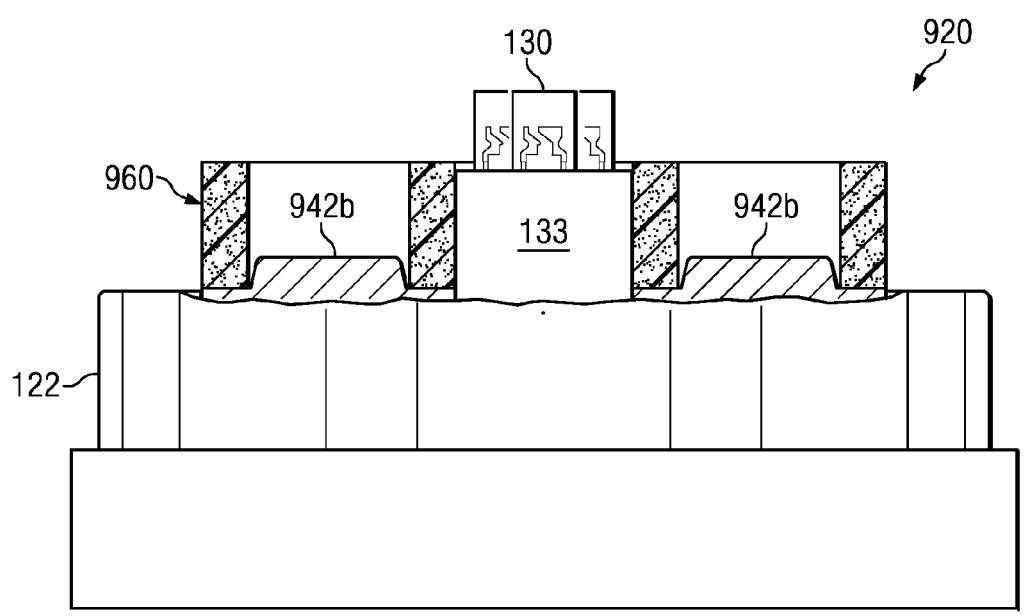
FIG. 11 shows a partial cross-sectional view of the assembled base unit and fragrance disk taken along section lines 11-11 in FIG. 10.

Turning next to FIGS. 9 through 11, an alternative embodiment of the base unit of the fragrance producing lighting device is shown and generally designated as base unit 920. FIGS. 9 through 11 also show an alternative embodiment of the fragrance disk, which is shown and generally designated as fragrance disk 960. FIG. 9 shows an exploded perspective view of the base unit 920 and fragrance disk 960, while FIG. 10 shows a perspective assembled view of the base unit 920 and the fragrance disk 960.

FIG. 11 shows a partial cross-sectional view of the assembled base unit 920 and fragrance disk 960 taken along section lines 11-11 in FIG. 10. The base unit 920 and fragrance disk 960 can be used, for example, with the fragrance producing lighting device 100 in place of the base unit 120 and fragrance disk 160, or with other embodiments described herein.

The base unit 920 can include components that are substantially the same as components of the base unit 920, and therefore have been given the same respective element numbers. The following description of base unit 920 is primarily directed to differences of the base unit 920 as compared with the base unit 120. Also, the fragrance disk 960 can be substantially the same as other embodiments of the fragrance disk described herein, except for specific differences discussed below.

The base unit 920 includes an electric heating element 940. The electric heating element 940 can be substantially the same as other embodiments of the heating element described herein, except that the upper surface of the heating element 940 is non-planar. For example, in the illustrated embodiment, the heating element 940 includes a plurality of surface features in the form of ridges 942a and 942b that extend radially between the post 133 and the housing 122. In the illustrated embodiment, the ridges 942b are wider than the ridges 942a, showing how the sizes and shapes of the surface features can vary from each other. While ridges 942 having rectangular cross-sectional shapes are shown, surface features having other cross-sectional shapes can be used. While surface features having a radial pattern are shown, other patterns can be used. For example, coaxial semi-circular ridges can be formed that are concentrically spaced between the post 133 and the housing 122. Alternatively, surface features can be formed that are in irregular patterns or in patterns that form recognizable images, such as in the shape of a flower or a smiling face. While the ridges 942 all have approximately the same height, in alternative embodiments the heights of the surface features can vary. Also, while the ridges 942 are all raised surface features, alternatively the heating element 940 can include recessed surface features exclusively or in combination with raised surface features.

The fragrance disk 960 includes a plurality of holes 961a and 961b that extend through the fragrance disk 960 as best shown in FIG. 11. The description of holes 161 applies equally to holes 961. However, the holes 961 are formed so as to mate with the surface features of the heating element 940 as best shown in FIG. 11. In the illustrated embodiment, the holes 961b are wider than the holes 961a so as to fit the ridges 942b and 942a, respectively. Thus, the raised surface features 942 at least partially extend into the holes 961 when the fragrance disk 960 is installed. This allows for an increased amount of surface-area contact between the fragrance disk 960 and the heating element 940 as compared to the heating element 140 and fragrance disk 160 of substantially the same size. This increased amount of surface-area contact can allow for increased and more evenly-distributed transfer of heat from the heating element 940 to the fragrance disk 960 as compared to the heating element 140 and fragrance disk 160. In embodiments where the heating element 140 includes recessed surface features, the fragrance disk 160 can be provided with raised features that mate with the recessed surface features of the heating element.

Also, in addition to the holes 961, which provide for venting as described above in connection with holes 161, the fragrance disk 960 can be provided with one or more recesses 963 about the outer peripheral side surface 965 thereof. The recesses allow for an increased amount of exposed surface area of the fragrance disk 960, thereby providing for a relatively increased amount of fragrance that can be released by the disk 960.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A device comprising:
   a base unit comprising:
      an annular heating surface defining a central heating surface hole;
      a post extending through the central heating surface hole; and
      a light source supported by the post; and
   an annular fragrance disk supported by the base unit,
   wherein the fragrance disk comprises a disk body that defines a central fragrance disk hole,
   wherein the fragrance disk includes a second hole extending through the disk body, and
   wherein the heating surface includes a raised surface feature configured to extend into the second hole in the fragrance disk.

2. The device of claim 1, wherein the raised surface feature is one of a plurality of raised surface features on the heating surface.

3. The device of claim 2, wherein the second hole is one of a plurality of holes in the disk body of the fragrance disk.

4. The device of claim 3, wherein each of the plurality of raised surface features is configured to extend into one of the holes in the disk body of the fragrance disk.

5. The device of claim 4, wherein each of the plurality of raised surface features is configured to extend into respective holes in the fragrance disk.

6. The device of claim 1, wherein the fragrance disk further includes a peripheral outer surface, wherein at least one recess is formed in the peripheral outer surface.

7. The device of claim 1, wherein the light source comprises a plurality of light emitting diodes, and wherein the base unit further comprises at least one electric resistive heating element for heating the heating surface.

* * * * *